US009421013B2

(12) United States Patent
Patel et al.

(10) Patent No.: US 9,421,013 B2
(45) Date of Patent: Aug. 23, 2016

(54) SURGICAL FASTENING APPARATUS

(71) Applicant: Covidien LP, Mansfield, MA (US)

(72) Inventors: Nihir Patel, Stamford, CT (US); Thomas Wenchell, Durham, CT (US)

(73) Assignee: Covidien LP, Mansfield, MA (US)

( * ) Notice: Subject to any disclaimer, the term of this patent is extended or adjusted under 35 U.S.C. 154(b) by 638 days.

(21) Appl. No.: 13/854,383

(22) Filed: Apr. 1, 2013

(65) Prior Publication Data

US 2013/0214028 A1   Aug. 22, 2013

Related U.S. Application Data

(63) Continuation of application No. 12/899,651, filed on Oct. 7, 2010, now Pat. No. 8,430,292.

(60) Provisional application No. 61/326,292, filed on Apr. 21, 2010, provisional application No. 61/255,529, filed on Oct. 28, 2009.

(51) Int. Cl.
| *A61B 17/068* | (2006.01) |
| *A61B 17/115* | (2006.01) |
| *A61B 17/064* | (2006.01) |
| *A61B 17/11* | (2006.01) |
| *A61B 17/3205* | (2006.01) |
| *A61B 17/072* | (2006.01) |

(52) U.S. Cl.
CPC .............. *A61B 17/068* (2013.01); *A61B 17/115* (2013.01); *A61B 17/1155* (2013.01); *A61B 17/0643* (2013.01); *A61B 17/1114* (2013.01); *A61B 17/32053* (2013.01); *A61B 2017/07242* (2013.01)

(58) Field of Classification Search
None
See application file for complete search history.

(56) References Cited

U.S. PATENT DOCUMENTS

| 3,193,165 | A | 7/1965 | Akhalaya et al. |
| 3,388,847 | A | 6/1968 | Kasulin et al. |
| 3,552,626 | A | 1/1971 | Astafiev |
| 3,638,652 | A | 2/1972 | Kelley |
| 3,771,526 | A | 11/1973 | Rudie |
| 4,198,982 | A | 4/1980 | Fortner et al. |
| 4,207,898 | A | 6/1980 | Becht |

(Continued)

FOREIGN PATENT DOCUMENTS

| CA | 908529 | 8/1972 |
| DE | 1057729 | 5/1959 |

(Continued)

OTHER PUBLICATIONS

Australian Examination Report dated Jun. 23, 2015 issued in Australian Application No. 2010236033.

(Continued)

*Primary Examiner* — Hemant M Desai
*Assistant Examiner* — Tanzim Imam

(57) ABSTRACT

A surgical fastening apparatus including a fastener receiving frame including a plurality of spaced apart openings formed therein and a fastener supporting member containing a plurality of surgical fasteners extending therefrom. The surgical fasteners are engagable with the plurality of openings to mate with the fastener receiving frame to fasten tissue therebetween. The fasteners are engageable with the openings in a plurality of positions dependent on a tissue thickness between the fastener receiving frame and the fastener supporting member.

20 Claims, 12 Drawing Sheets

(56) References Cited

U.S. PATENT DOCUMENTS

| | | | |
|---|---|---|---|
| 4,289,133 A | 9/1981 | Rothfuss | |
| 4,304,236 A | 12/1981 | Conta et al. | |
| 4,319,576 A | 3/1982 | Rothfuss | |
| 4,350,160 A | 9/1982 | Kolesov et al. | |
| 4,351,466 A | 9/1982 | Noiles | |
| 4,379,457 A | 4/1983 | Gravener et al. | |
| 4,473,077 A | 9/1984 | Noiles et al. | |
| 4,476,863 A | 10/1984 | Kanshin et al. | |
| 4,485,817 A | 12/1984 | Swiggett | |
| 4,488,523 A | 12/1984 | Shichman | |
| 4,505,272 A | 3/1985 | Utyamyshev et al. | |
| 4,505,414 A | 3/1985 | Filipi | |
| 4,520,817 A | 6/1985 | Green | |
| 4,550,870 A | 11/1985 | Krumme et al. | |
| 4,573,468 A | 3/1986 | Conta et al. | |
| 4,576,167 A | 3/1986 | Noiles | |
| 4,592,354 A | 6/1986 | Rothfuss | |
| 4,603,693 A | 8/1986 | Conta et al. | |
| 4,606,343 A | 8/1986 | Conta et al. | |
| 4,646,745 A | 3/1987 | Noiles | |
| 4,665,917 A | 5/1987 | Clanton et al. | |
| 4,667,673 A | 5/1987 | Li | |
| 4,671,445 A | 6/1987 | Barker et al. | |
| 4,700,703 A | 10/1987 | Resnick et al. | |
| 4,703,887 A | 11/1987 | Clanton et al. | |
| 4,708,141 A | 11/1987 | Inoue et al. | |
| 4,717,063 A | 1/1988 | Ebihara | |
| 4,752,024 A | 6/1988 | Green et al. | |
| 4,754,909 A | 7/1988 | Barker et al. | |
| 4,776,506 A | 10/1988 | Green | |
| 4,817,847 A | 4/1989 | Redtenbacher et al. | |
| 4,873,977 A | 10/1989 | Avant et al. | |
| 4,893,622 A | 1/1990 | Green et al. | |
| 4,903,697 A | 2/1990 | Resnick et al. | |
| 4,907,591 A | 3/1990 | Vasconcellos et al. | |
| 4,917,114 A | 4/1990 | Green et al. | |
| 4,957,499 A | 9/1990 | Lipatov et al. | |
| 4,962,877 A | 10/1990 | Hervas | |
| 5,005,749 A | 4/1991 | Aranyi | |
| 5,042,707 A | 8/1991 | Taheri | |
| 5,047,039 A | 9/1991 | Avant et al. | |
| 5,104,025 A | 4/1992 | Main et al. | |
| 5,119,983 A | 6/1992 | Green et al. | |
| 5,122,156 A | 6/1992 | Granger et al. | |
| 5,139,513 A | 8/1992 | Segato | |
| 5,158,222 A | 10/1992 | Green et al. | |
| 5,188,638 A | 2/1993 | Tzakis | |
| 5,193,731 A | 3/1993 | Aranyi | |
| 5,197,648 A | 3/1993 | Gingold | |
| 5,197,649 A | 3/1993 | Bessler et al. | |
| 5,205,459 A | 4/1993 | Brinkerhoff et al. | |
| 5,221,036 A | 6/1993 | Takase | |
| 5,222,963 A * | 6/1993 | Brinkerhoff | A61B 17/11 227/179.1 |
| 5,253,793 A | 10/1993 | Green et al. | |
| 5,261,920 A | 11/1993 | Main et al. | |
| 5,271,543 A | 12/1993 | Grant et al. | |
| 5,271,544 A | 12/1993 | Fox et al. | |
| 5,275,322 A | 1/1994 | Brinkerhoff et al. | |
| 5,282,810 A | 2/1994 | Allen et al. | |
| 5,285,944 A | 2/1994 | Green et al. | |
| 5,285,945 A | 2/1994 | Brinkerhoff et al. | |
| 5,292,053 A | 3/1994 | Bilotti et al. | |
| 5,309,927 A | 5/1994 | Welch | |
| 5,312,024 A | 5/1994 | Grant et al. | |
| 5,314,435 A | 5/1994 | Green et al. | |
| 5,314,436 A | 5/1994 | Wilk | |
| 5,330,486 A | 7/1994 | Wilk | |
| 5,333,773 A | 8/1994 | Main et al. | |
| 5,344,059 A | 9/1994 | Green et al. | |
| 5,346,115 A | 9/1994 | Perouse et al. | |
| 5,348,259 A | 9/1994 | Blanco et al. | |
| 5,350,104 A | 9/1994 | Main et al. | |
| 5,355,897 A | 10/1994 | Pietrafitta et al. | |
| 5,360,154 A | 11/1994 | Green | |
| 5,368,215 A | 11/1994 | Green et al. | |
| 5,392,979 A | 2/1995 | Green et al. | |
| 5,395,030 A | 3/1995 | Kuramoto et al. | |
| 5,403,333 A | 4/1995 | Kaster et al. | |
| 5,404,870 A | 4/1995 | Brinkerhoff et al. | |
| 5,411,508 A | 5/1995 | Bessler et al. | |
| 5,425,738 A | 6/1995 | Gustafson et al. | |
| 5,433,721 A | 7/1995 | Hooven et al. | |
| 5,437,684 A | 8/1995 | Calabrese et al. | |
| 5,439,156 A | 8/1995 | Grant et al. | |
| 5,443,198 A | 8/1995 | Viola et al. | |
| 5,447,514 A | 9/1995 | Gerry et al. | |
| 5,454,825 A | 10/1995 | Van Leeuwen et al. | |
| 5,464,415 A | 11/1995 | Chen | |
| 5,470,006 A | 11/1995 | Rodak | |
| 5,474,223 A | 12/1995 | Viola et al. | |
| 5,497,934 A | 3/1996 | Brady et al. | |
| 5,503,635 A | 4/1996 | Sauer et al. | |
| 5,522,534 A | 6/1996 | Viola et al. | |
| 5,533,661 A | 7/1996 | Main et al. | |
| 5,588,579 A | 12/1996 | Schnut et al. | |
| 5,609,285 A | 3/1997 | Grant et al. | |
| 5,626,591 A | 5/1997 | Kockerling et al. | |
| 5,632,433 A | 5/1997 | Grant et al. | |
| 5,639,008 A | 6/1997 | Gallagher et al. | |
| 5,641,111 A | 6/1997 | Ahrens et al. | |
| 5,658,300 A | 8/1997 | Bito et al. | |
| 5,669,918 A | 9/1997 | Balazs et al. | |
| 5,685,474 A | 11/1997 | Seeber | |
| 5,709,335 A | 1/1998 | Heck | |
| 5,715,987 A | 2/1998 | Kelley et al. | |
| 5,718,360 A | 2/1998 | Green et al. | |
| 5,720,755 A | 2/1998 | Dakov | |
| 5,732,872 A | 3/1998 | Bolduc et al. | |
| 5,749,896 A | 5/1998 | Cook | |
| 5,758,814 A | 6/1998 | Gallagher et al. | |
| 5,799,857 A | 9/1998 | Robertson et al. | |
| 5,814,055 A | 9/1998 | Knodel et al. | |
| 5,833,698 A | 11/1998 | Hinchliffe et al. | |
| 5,836,503 A | 11/1998 | Ehrenfels et al. | |
| 5,839,639 A | 11/1998 | Sauer et al. | |
| 5,855,312 A | 1/1999 | Toledano | |
| 5,860,581 A | 1/1999 | Robertson et al. | |
| 5,868,760 A | 2/1999 | McGuckin, Jr. | |
| 5,881,943 A | 3/1999 | Heck et al. | |
| 5,915,616 A | 6/1999 | Viola et al. | |
| 5,947,363 A | 9/1999 | Bolduc et al. | |
| 5,951,576 A | 9/1999 | Wakabayashi | |
| 5,957,363 A | 9/1999 | Heck | |
| 5,993,468 A | 11/1999 | Rygaard | |
| 6,024,748 A | 2/2000 | Manzo et al. | |
| 6,050,472 A | 4/2000 | Shibata | |
| 6,053,390 A | 4/2000 | Green et al. | |
| 6,068,636 A | 5/2000 | Chen | |
| 6,083,241 A | 7/2000 | Longo et al. | |
| 6,102,271 A | 8/2000 | Longo et al. | |
| 6,117,148 A | 9/2000 | Ravo et al. | |
| 6,119,913 A | 9/2000 | Adams et al. | |
| 6,126,058 A | 10/2000 | Adams et al. | |
| 6,142,933 A | 11/2000 | Longo et al. | |
| 6,149,667 A | 11/2000 | Hovland et al. | |
| 6,176,413 B1 | 1/2001 | Heck et al. | |
| 6,179,195 B1 | 1/2001 | Adams et al. | |
| 6,193,129 B1 | 2/2001 | Bittner et al. | |
| 6,203,553 B1 | 3/2001 | Robertson et al. | |
| 6,209,773 B1 | 4/2001 | Bolduc et al. | |
| 6,241,140 B1 | 6/2001 | Adams et al. | |
| 6,253,984 B1 | 7/2001 | Heck et al. | |
| 6,258,107 B1 | 7/2001 | Balázs et al. | |
| 6,264,086 B1 | 7/2001 | McGuckin, Jr. | |
| 6,269,997 B1 | 8/2001 | Balázs et al. | |
| 6,273,897 B1 | 8/2001 | Dalessandro et al. | |
| 6,279,809 B1 | 8/2001 | Nicolo | |
| 6,302,311 B1 | 10/2001 | Adams et al. | |
| 6,338,737 B1 | 1/2002 | Toledano | |
| 6,343,731 B1 | 2/2002 | Adams et al. | |
| 6,387,105 B1 | 5/2002 | Gifford, III et al. | |
| 6,398,795 B1 | 6/2002 | McAlister et al. | |
| 6,402,008 B1 | 6/2002 | Lucas | |

(56) References Cited

U.S. PATENT DOCUMENTS

| | | |
|---|---|---|
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 * | 1/2003 | Huxel ............... A61B 17/0643 227/179.1 |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 7,032,798 B2 | 4/2006 | Whitman et al. |
| 7,059,331 B2 | 6/2006 | Adams et al. |
| 7,059,510 B2 | 6/2006 | Orban, III |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,303,106 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,338,505 B2 | 3/2008 | Belson |
| 7,364,060 B2 | 4/2008 | Milliman |
| 7,398,908 B2 | 7/2008 | Holsten et al. |
| 7,399,305 B2 | 7/2008 | Csiky et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,442,201 B2 | 10/2008 | Pugsley et al. |
| 7,455,676 B2 | 11/2008 | Holsten et al. |
| 7,455,682 B2 | 11/2008 | Viola |
| 7,481,349 B2 | 1/2009 | Holsten et al. |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,717,313 B2 | 5/2010 | Criscuolo et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,080 B2 | 11/2010 | Schwemberger |
| 7,845,536 B2 | 12/2010 | Viola et al. |
| 2001/1000090 | 5/2001 | Heck et al. |
| 2001/0010320 A1 | 8/2001 | Bolduc et al. |
| 2001/0054636 A1 | 12/2001 | Nicolo |
| 2002/1002073 | 2/2002 | Adams et al. |
| 2002/0047036 A1 | 4/2002 | Sullivan et al. |
| 2002/0058955 A1 | 5/2002 | Blatter et al. |
| 2002/1006314 | 5/2002 | Adams et al. |
| 2002/0185516 A1 | 12/2002 | Heck et al. |
| 2002/0185517 A1 | 12/2002 | Vresh et al. |
| 2003/0019905 A1 | 1/2003 | Adams et al. |
| 2003/0047582 A1 | 3/2003 | Sonnenschein et al. |
| 2003/0057251 A1 | 3/2003 | Hartwick |
| 2003/0065342 A1 | 4/2003 | Nobis et al. |
| 2003/0073981 A1 | 4/2003 | Whitman et al. |
| 2003/0089757 A1 | 5/2003 | Whitman |
| 2003/0111507 A1 | 6/2003 | Nunez |
| 2003/0127491 A1 | 7/2003 | Adams et al. |
| 2003/0132267 A1 | 7/2003 | Adams et al. |
| 2003/0144675 A1 * | 7/2003 | Nicolo ............... A61B 17/0643 606/153 |
| 2003/0178465 A1 | 9/2003 | Bilotti et al. |
| 2003/0183671 A1 | 10/2003 | Mooradian et al. |
| 2003/0192936 A1 | 10/2003 | Hartwick |
| 2003/0192937 A1 | 10/2003 | Sullivan et al. |
| 2003/0201301 A1 | 10/2003 | Bolduc et al. |

(56) References Cited

U.S. PATENT DOCUMENTS

| | | |
|---|---|---|
| 2003/0220660 A1* | 11/2003 | Kortenbach ....... A61B 17/0643 606/151 |
| 2003/1021804 | 11/2003 | Sharma et al. |
| 2003/1022211 | 12/2003 | Orban, III |
| 2004/0092960 A1 | 5/2004 | Abrams et al. |
| 2004/0092974 A1 | 5/2004 | Gannoe et al. |
| 2004/0118896 A1 | 6/2004 | Sharma et al. |
| 2004/0134964 A1 | 7/2004 | Adams et al. |
| 2004/0153124 A1 | 8/2004 | Whitman |
| 2004/0232198 A1 | 11/2004 | Adams et al. |
| 2005/0051597 A1 | 3/2005 | Tolendano |
| 2005/1006745 | 3/2005 | Vresh et al. |
| 2005/0087580 A1 | 4/2005 | Orban, III |
| 2005/0107813 A1 | 5/2005 | Gilete Garcia |
| 2005/0116009 A1 | 6/2005 | Milliman |
| 2005/0125009 A1 | 6/2005 | Perry et al. |
| 2005/0143758 A1 | 6/2005 | Abbott et al. |
| 2005/0145674 A1 | 7/2005 | Sonnenschein et al. |
| 2005/0145675 A1 | 7/2005 | Hartwick et al. |
| 2006/0000869 A1 | 1/2006 | Fontayne |
| 2006/0011698 A1 | 1/2006 | Okada et al. |
| 2006/0047307 A1 | 3/2006 | Ortiz et al. |
| 2006/0047308 A1 | 3/2006 | Ortiz et al. |
| 2006/0085032 A1 | 4/2006 | Viola |
| 2006/0085033 A1 | 4/2006 | Criscuolo et al. |
| 2006/0085034 A1 | 4/2006 | Bettuchi |
| 2006/0085035 A1 | 4/2006 | Viola |
| 2006/0097025 A1 | 5/2006 | Milliman et al. |
| 2006/0108393 A1 | 5/2006 | Heinrich et al. |
| 2006/0144897 A1 | 7/2006 | Jankowski et al. |
| 2006/0151567 A1 | 7/2006 | Roy |
| 2006/0191975 A1 | 8/2006 | Adams et al. |
| 2006/0201989 A1 | 9/2006 | Ojeda |
| 2006/0201993 A1 | 9/2006 | Hur |
| 2006/0241692 A1 | 10/2006 | McGuckin, Jr. et al. |
| 2006/0255090 A1 | 11/2006 | Milliman et al. |
| 2006/0289601 A1 | 12/2006 | Orban, III |
| 2007/0023475 A1 | 2/2007 | Csiky |
| 2007/0027473 A1 | 2/2007 | Vresh et al. |
| 2007/0029363 A1 | 2/2007 | Popov |
| 2007/0034666 A1 | 2/2007 | Holsten et al. |
| 2007/0034667 A1 | 2/2007 | Holsten et al. |
| 2007/0034668 A1 | 2/2007 | Holsten et al. |
| 2007/0038248 A1 | 2/2007 | Heinrch |
| 2007/0060952 A1 | 3/2007 | Roby et al. |
| 2008/0058865 A1 | 3/2008 | Wilk |
| 2008/0114385 A1* | 5/2008 | Byrum ................ A61B 17/11 606/154 |
| 2008/0149685 A1 | 6/2008 | Smith et al. |
| 2009/0001121 A1 | 1/2009 | Hess et al. |
| 2009/0212088 A1 | 8/2009 | Okada et al. |
| 2009/0236388 A1 | 9/2009 | Cole et al. |
| 2009/0236389 A1 | 9/2009 | Cole et al. |
| 2009/0236390 A1 | 9/2009 | Cole et al. |
| 2009/0236391 A1 | 9/2009 | Cole et al. |
| 2009/0236392 A1 | 9/2009 | Cole et al. |
| 2009/0236394 A1 | 9/2009 | Cole et al. |
| 2009/0236396 A1 | 9/2009 | Cole et al. |
| 2009/0236397 A1 | 9/2009 | Cole et al. |
| 2009/0236400 A1 | 9/2009 | Cole et al. |
| 2009/1023017 | 9/2009 | Milliman |
| 2009/1023639 | 9/2009 | Cole et al. |
| 2009/1023640 | 9/2009 | Cole et al. |
| 2009/0242612 A1 | 10/2009 | Adams et al. |
| 2009/0250502 A1 | 10/2009 | Milliman |
| 2009/0255976 A1 | 10/2009 | Marczyk et al. |
| 2009/1030208 | 12/2009 | Harari et al. |
| 2009/1032149 | 12/2009 | Holsten et al. |
| 2010/0001036 A1 | 1/2010 | Marczyk et al. |
| 2010/0001037 A1 | 1/2010 | Racenet et al. |
| 2010/0019016 A1 | 1/2010 | Edoga et al. |
| 2010/0025452 A1 | 2/2010 | Whitman |
| 2010/0038401 A1 | 2/2010 | Milliman et al. |
| 2010/0051668 A1 | 3/2010 | Milliman et al. |
| 2010/0059571 A1 | 3/2010 | Chen et al. |
| 2010/0065609 A1 | 3/2010 | Schwemberger |
| 2010/1006560 | 3/2010 | Orban, III et al. |
| 2010/0084453 A1 | 4/2010 | Hu |
| 2010/0089971 A1 | 4/2010 | Milliman et al. |
| 2010/0096435 A1 | 4/2010 | Fuchs et al. |
| 2010/0108739 A1 | 5/2010 | Holsten et al. |
| 2010/0108740 A1 | 5/2010 | Pastorelli et al. |
| 2010/0108741 A1 | 5/2010 | Hessler et al. |
| 2010/0127039 A1 | 5/2010 | Hessler et al. |
| 2010/0133319 A1 | 6/2010 | Milliman et al. |
| 2010/0147923 A1 | 6/2010 | D'Agostino et al. |
| 2010/0155452 A1 | 6/2010 | Csiky |
| 2010/0155454 A1 | 6/2010 | Viola |
| 2010/0163598 A1 | 7/2010 | Belzer |
| 2010/0170932 A1 | 7/2010 | Wenchell et al. |
| 2010/0224668 A1 | 9/2010 | Fontayne et al. |
| 2010/0230465 A1 | 9/2010 | Smith et al. |
| 2010/0230466 A1 | 9/2010 | Criscuolo et al. |
| 2010/0230467 A1 | 9/2010 | Criscuolo et al. |
| 2010/0237132 A1 | 9/2010 | Measamer et al. |
| 2010/0258611 A1 | 10/2010 | Smith et al. |
| 2010/0264195 A1 | 10/2010 | Bettuchi |
| 2010/0270356 A1 | 10/2010 | Holsten et al. |
| 2010/0276471 A1 | 11/2010 | Whitman |
| 2010/0282813 A1 | 11/2010 | Milliman |
| 2010/0282815 A1 | 11/2010 | Bettuchi et al. |
| 2010/0301098 A1 | 12/2010 | Kostrzewski |

FOREIGN PATENT DOCUMENTS

| | | |
|---|---|---|
| DE | 3301713 | 11/1989 |
| EP | 0152382 | 8/1985 |
| EP | 0173451 | 3/1986 |
| EP | 0190022 | 8/1986 |
| EP | 282157 | 9/1988 |
| EP | 0517488 | 6/1992 |
| EP | 0503689 | 9/1992 |
| EP | 1728475 | 12/2006 |
| EP | 2030578 | 3/2009 |
| FR | 1461464 | 12/1966 |
| FR | 1588250 | 4/1970 |
| FR | 2443239 | 12/1979 |
| GB | 1185292 | 3/1970 |
| GB | 2016991 | 9/1979 |
| GB | 2070499 | 9/1981 |
| JP | 1310652 | 12/1989 |
| JP | 4309341 B2 | 8/2009 |
| NL | 7711347 | 10/1977 |
| WO | 8706448 | 11/1987 |
| WO | 8900406 | 1/1989 |
| WO | 9006085 | 6/1990 |
| WO | WO 2004/112583 | 12/2004 |
| WO | WO 2006/044810 | 4/2006 |
| WO | WO 2007/080111 | 7/2007 |
| WO | WO 2008/007377 | 1/2008 |

OTHER PUBLICATIONS

Japanese Office Action dated May 29, 2015 issued in Japanese Application No. 2014-161010.

European Search Report dated Mar. 3, 2011 in related European Application No. 10 25 1855.

European Search Report dated Feb. 7, 2012 in related European Application No. 11 00 9512.

Japanese Examination Report dated Mar. 10, 2014 in related Japanese Application No. 2010-241566.

Canadian Office Action dated Jun. 1, 2016, issued in Canadian Application No. 2,718,091.

* cited by examiner

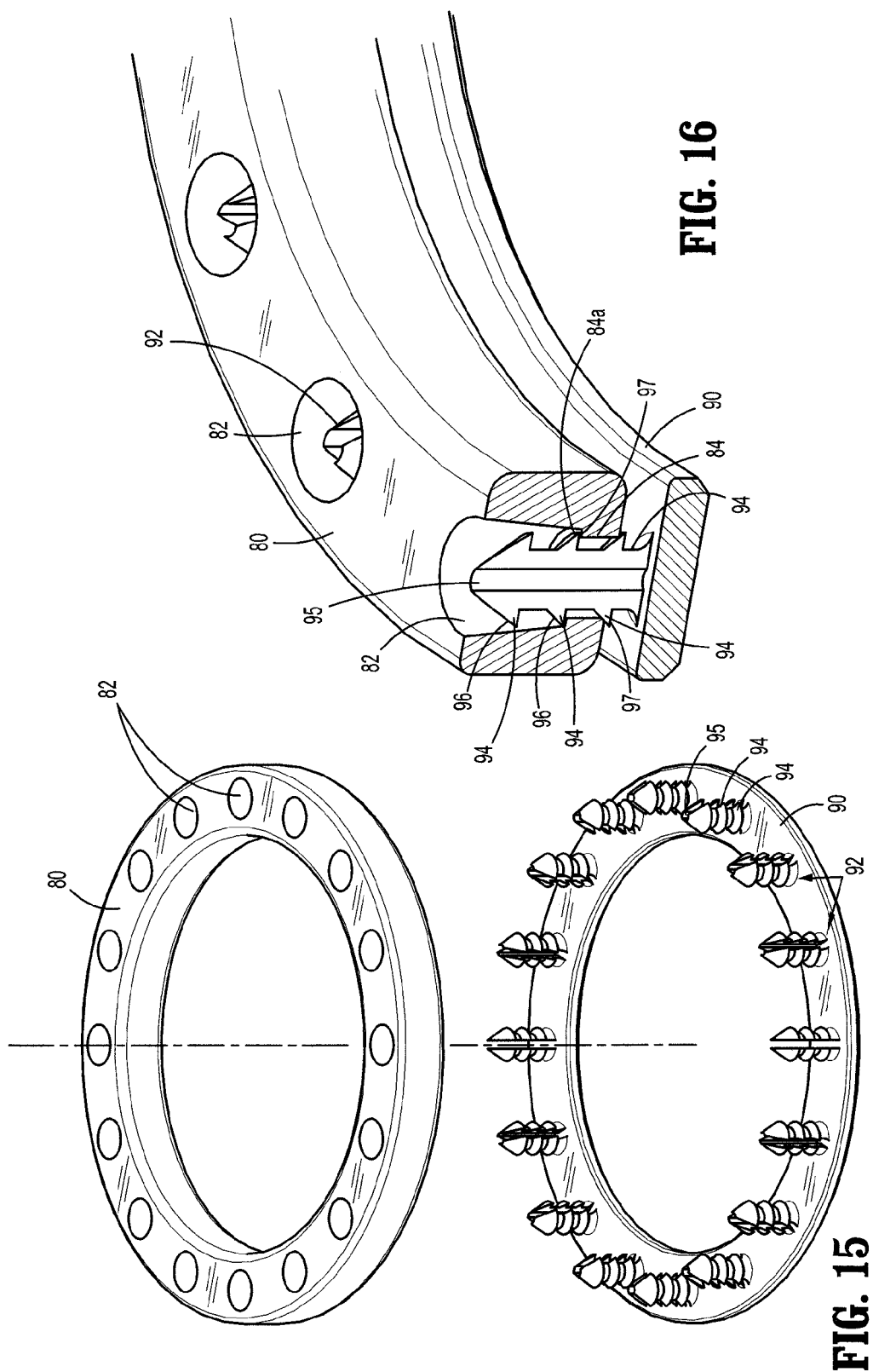

SURGICAL FASTENING APPARATUS

This application is a continuation of U.S. application Ser. No. 12/899,651 filed Oct. 7, 2010, now U.S. Pat. No. 8,430,292, which claims priority from provisional application Ser. No. 61/326,292, filed Apr. 21, 2010 and priority from provisional application Ser. No. 60/255,529, filed Oct. 28, 2009. The entire contents of each of these applications are incorporated herein by reference.

BACKGROUND

1. Technical Field

The present disclosure relates to a surgical fastening apparatus and, more particularly, to a surgical fastening apparatus having a fastener and retainer system.

2. Background of the Related Art

Various types of surgical stapling instruments for performing a circular anastomosis are well known, wherein an operator actuates the apparatus at a location which is relatively remote from the location at which the circular anastomosis takes place. Anastomosis is the surgical joining of separate hollow organ sections. Typically, an anastomosis procedure involves surgery in which a diseased or defective section of hollow tissue is removed.

A conventional surgical stapling instrument for performing a circular anastomosis in a hemorrhoidal or other surgical procedure generally includes a shell assembly having an annular array of staples and staple slots and an anvil assembly having a circular array of staple forming pockets in a proximal surface thereof. An example of surgical stapling instruments for performing circular anastomosis is described in U.S. Pat. Nos. 7,168,604, 7,303,106 and pending U.S. application Ser. No. 12/550,443, filed Aug. 31, 2009, all of which are incorporated herein in their entirety by reference. Typically, the anvil assembly is longitudinally movable from an open position to a closed position which places the anvil assembly adjacent to the shell assembly to clamp the body tissue therebetween. After bringing the anvil and shell assemblies to a closed position to clamp tissue, an annular pusher including a plurality of pushers which are configured to eject a corresponding staple from the staple slot through the tissue and against a receiving pocket of the anvil to form staples is actuated by the operator in a relatively remote region to perform a circular anastomosis. After stapling the tissues together, the tissue is severed by the annular blade and extracted.

Surgical fastening instruments applying two part surgical fasteners are known. In these instruments, a plurality of retainers are supported in an anvil assembly and a plurality of fasteners are supported in a fastener holding assembly. The fasteners are advanced through tissue and into engagement with openings in respective retainers. These two part fasteners are typically composed of resorbable material. The firing force of the fasteners in some of these instruments could shift the retainers out of position which may result in misalignment. In addition, the retainers may slip against the anvil and/or may come off the anvil before firing which may also result in misalignment. Accordingly, it would be advantageous to provide a configuration which enhances mating of the fasteners and the retainers and it may be useful to provide such configuration in a circular anastomosis instrument.

Additionally, the thickness of the clamped tissue can vary in different regions. Therefore, it would be advantageous to provide a fastener-retainer configuration which can accommodate such varying tissue thickness.

SUMMARY

In accordance with one aspect of the present disclosure, a surgical fastening apparatus is provided including a fastener receiving frame including a plurality of spaced apart openings formed therein and a fastener supporting member having a plurality of spaced apart surgical fasteners extending therefrom. The surgical fasteners are engagable with the plurality of openings to mate with the fastener receiving frame to fasten tissue therebetween, the fasteners engageable with the openings in a plurality of positions dependent on a tissue thickness between the fastener receiving frame and the fastener supporting member.

The fastener receiving frame is preferably detachably secured to a supporting structure of the surgical apparatus. Preferably, a pusher advances the fastener supporting member into engagement with the fastener receiving frame.

In a preferred embodiment, the pusher is an annular pusher and the fastener supporting member includes an annular supporting frame. Preferably, an annular blade advanceable by the annular pusher to sever tissue is provided.

In some embodiments, the fasteners each have a series of locking tabs spaced axially along the fasteners to mate with the respective opening in the fastener receiving frame at various positions to provide a variable depth of engagement. In some embodiments, the openings can have a series of locking surfaces to engage the respective fastener at various positions to provide a variable depth of engagement. In one embodiment, the locking tabs include a plurality of substantially semi-circular ribs. In one embodiment, the locking tabs include a plurality of projections angled to enable movement of the fastener in a first direction toward the opening in the fastener receiving frame and prevent movement of the fastener in a second opposite direction away from the opening. The fasteners can include a longitudinally extending slot formed therein.

The fastener can include a reservoir to receive a drug.

In some embodiments, the opening in the fastener receiving frame has a first depth and the respective fastener has a first length, wherein the first length is less than the first depth.

In another aspect, the present disclosure provides a surgical fastening apparatus comprising a fastener receiving frame including a plurality of spaced apart openings formed therein and a fastener supporting member containing a plurality of spaced apart surgical fasteners extending therefrom. The surgical fasteners are engagable with the plurality of openings to mate with the fastener receiving frame to fasten tissue therebetween. The fasteners and openings are configured to allow locking engagement of the fasteners in the openings at two or more depths of the fastener, the depth of the fastener preselected prior to advancement of the fasteners into the openings.

Preferably, the fastener receiving frame is detachably secured to a supporting structure of the surgical apparatus and a substantially annular pusher advances the fastener supporting member into engagement with the fastener receiving frame. In preferred embodiments, the fastener supporting member and fastener receiving frame are substantially annular. The fasteners can include a series of locking tabs spaced axially along a length of the fastener.

In one embodiment, the surgical fastening apparatus includes a sensor positioned at a distal portion to determine a tissue parameter to send a signal to determine the extent of advancement of the fastener supporting member. In another embodiment, the surgical fastening apparatus includes a sensor positioned at the distal portion to determine an apparatus parameter to send a signal to determine the extent of advancement of the fastener supporting member.

The fastener receiving frame, fastener supporting member and/or plurality of fasteners can be made of biodegradable polymer. The fastener receiving frame and/or fastener supporting member can be elastic to provide flexibility.

BRIEF DESCRIPTION OF THE DRAWINGS

The above and other objects and features of the present disclosure will become apparent from the following description of embodiments given in conjunction with the accompanying drawings, in which:

FIG. 15 is a perspective view of a fastener receiving frame and fastener supporting member of an alternate embodiment of the present disclosure;

FIG. 16 is a close up cross-sectional view of a portion of the fastener receiving frame and fastener supporting member showing their locking engagement.

DETAILED DESCRIPTION OF THE EMBODIMENTS

Figure 1:
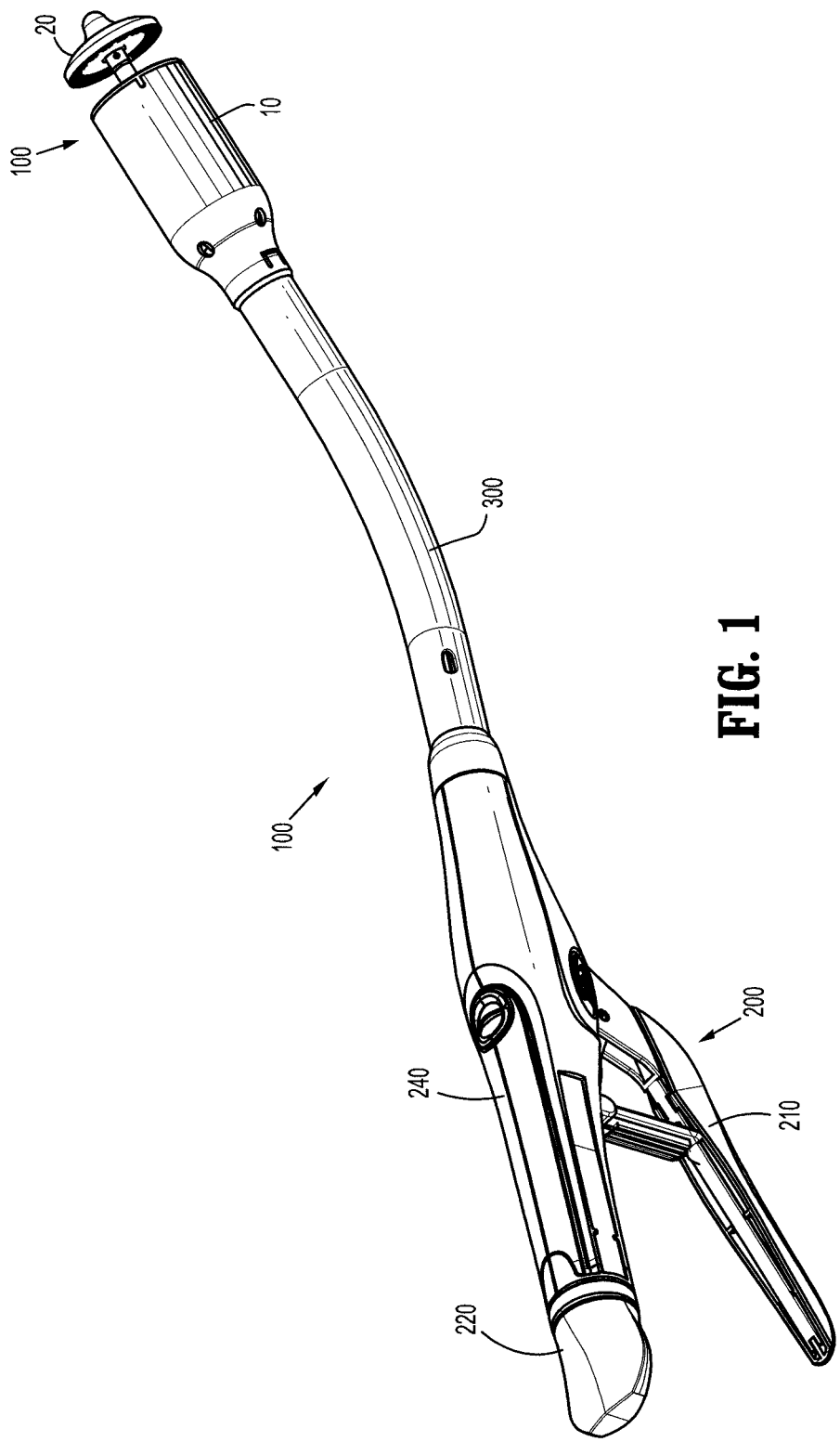
FIG. 1 is a perspective view of a surgical fastening apparatus in accordance with an embodiment of the present disclosure.

Various embodiments of the presently disclosed end effector will now be described in detail with reference to the drawings, wherein like references numerals identify similar or identical elements. In the drawings and in the description which follows, the term "proximal" will refer to the end of the component that is closer to the operator during use, while the term "distal" will refer to the end of the component that is further from the operator, as is traditional and conventional in the art.

With reference to FIG. 1, a surgical fastening apparatus 100 is illustrated. A suitable example of a surgical fastening apparatus 100 is disclosed in U.S. Pat. Nos. 7,168,604, 7,303,106 and pending U.S. application Ser. No. 12/550,443, filed Aug. 31, 2009, the entire contents of each are incorporated by reference herein. The surgical fastening apparatus 1000 includes a handle assembly 200, an elongate shaft 300 extending distally therefrom, and an end effector 100 coupled to the distal end of the elongate shaft 300. The length and the curvature of elongate shaft 300 may be tailored to meet the specific needs of surgical procedure being performed. Elongate shaft 300 alternatively may be flexible to facilitate maneuvering of surgical fastening apparatus 100, more specifically, end effector 100, to the targeted area in the body containing tissues to be joined.

The handle assembly 200 generally includes a stationary handle 240, a pivotable trigger 210 and a rotatable knob 220. When rotatable knob 220 is manually rotated, anvil assembly 20 will longitudinally translate in relation to shell assembly 10 between an open position and a closed position in a manner described below. Actuation of trigger 210 towards stationary handle 240 advances annular pusher 40 (FIG. 6) distally within shell assembly 10 to eject fasteners from shell assembly 10 in a manner described below. Actuation of trigger 210 also longitudinally translates a knife 51 (FIG. 6) that severs tissue as well as separates the formed fasteners from a retaining frame in a manner described below.

Figure 2:
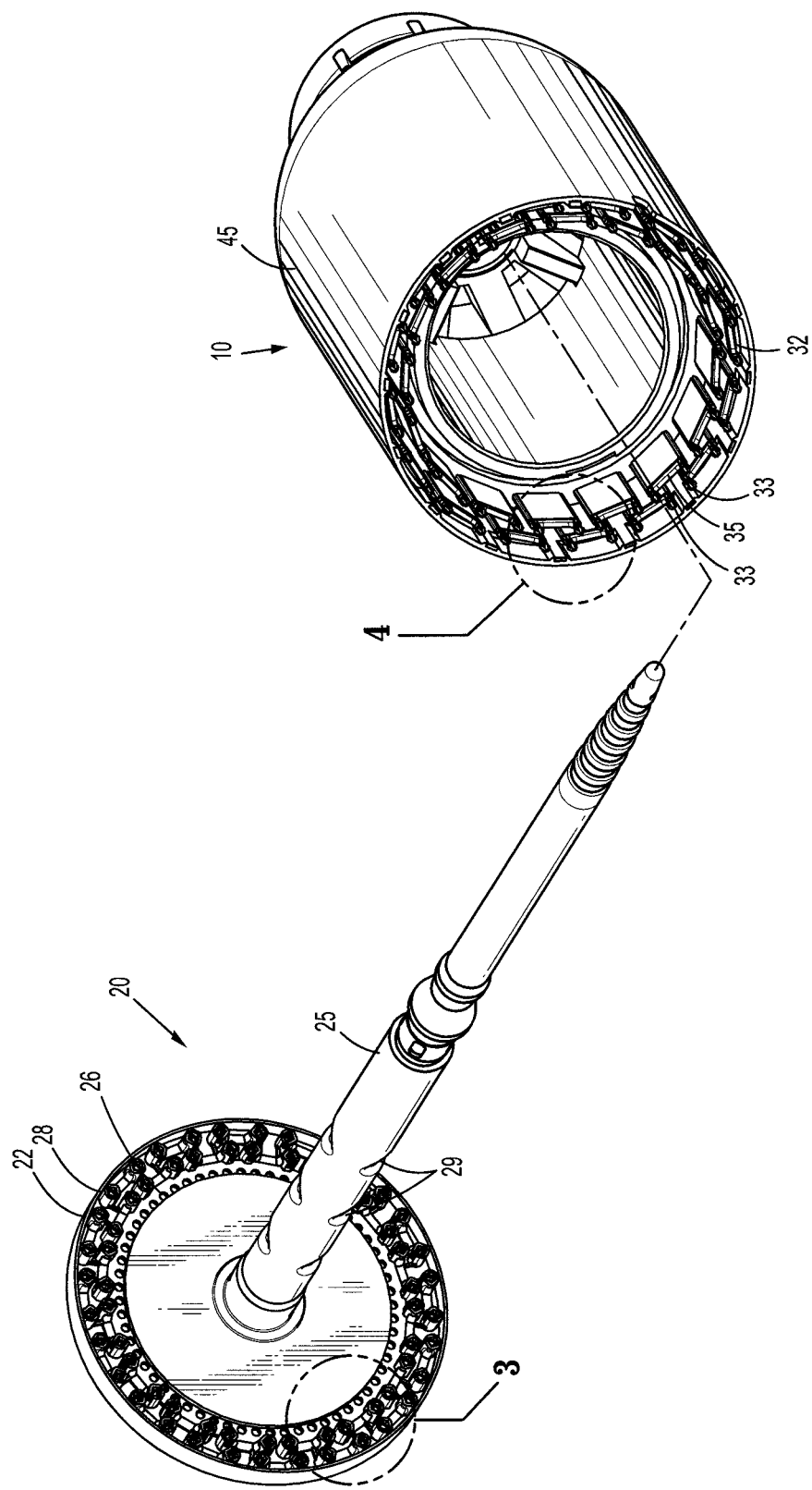
FIG. 2 is a perspective view of the end effector of FIG. 1.
Figure 6:
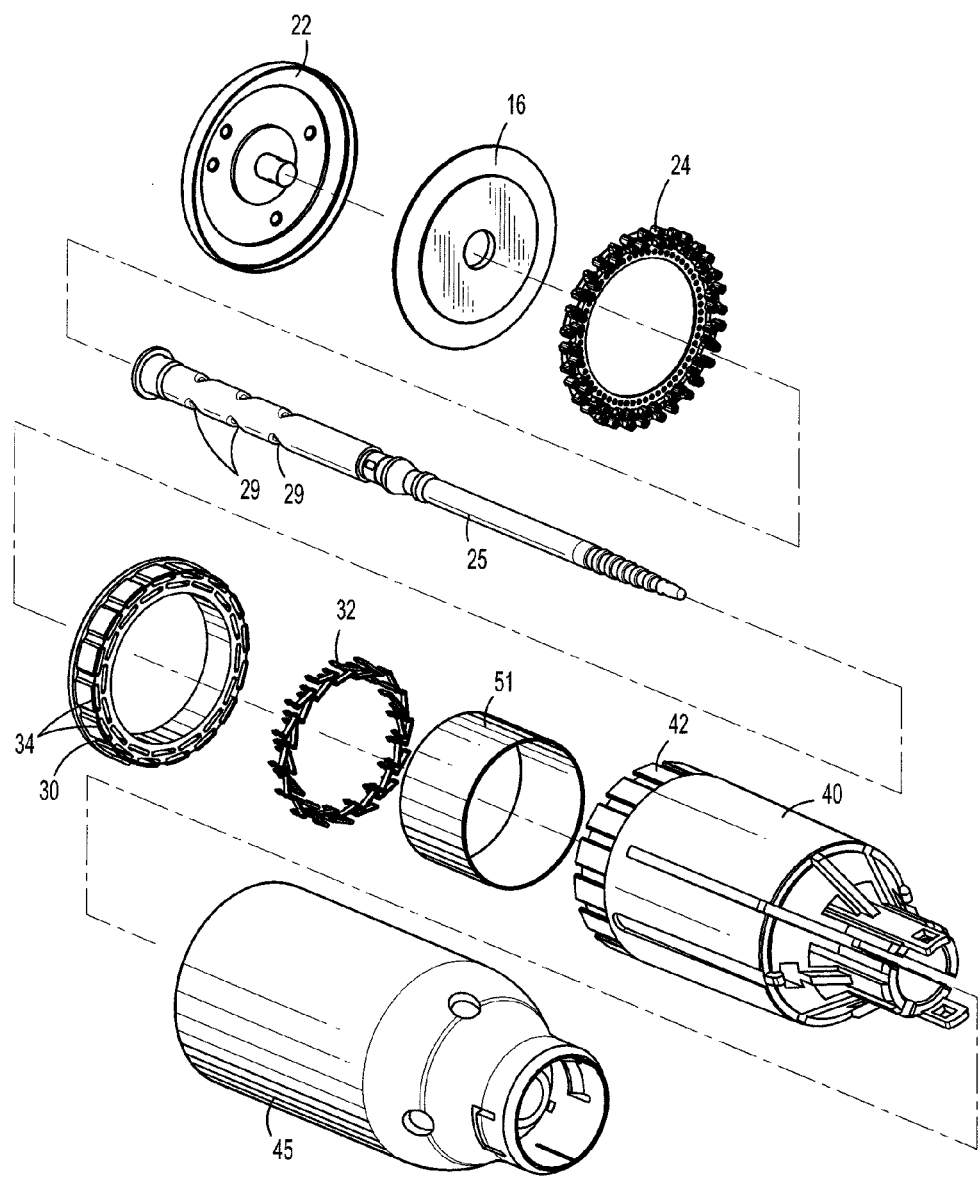
FIG. 6 is an exploded view of the end effector of FIG. 2.

Referring now to FIGS. 2 and 6, an embodiment of the present disclosure is shown generally as staple end effector 100. Staple end effector 100 includes an anvil assembly 20 and a shell assembly 10.

Anvil assembly 20 includes an anvil 22, fastener retaining frame 24, and a flange member 16. Flange member 16 is preferably composed of plastic material such as HDPE. As will be discussed in further detail below, fastener retaining frame 24 includes a plurality of perforations 26 and a plurality of retainers 28 (FIGS. 2 and 8) and is detachably secured to flange member 16 which is fixedly attached to anvil 22. Anvil shaft 25 extends from anvil 22 and can include a plurality of openings 29 for receipt of purse string suture such as described in detail in patent application Ser. No. 12/550,443, previously incorporated by reference herein in its entirety.

Shell assembly 10 accommodates therein a fastener guide member 30 which includes a plurality of axially extending and circumferentially arranged fastener slots 34 (FIG. 6) for receiving therein a plurality of axially extending surgical fasteners 32 having distally directed tissue piercing prongs for mating with the plurality of retainers 28 on fastener retaining frame 24 to fasten tissue therebetween. Shell assembly 10 further accommodates therein an annular pusher 40 including a plurality of pusher fingers 42 operably associated with the plurality of surgical fasteners 32. Each pusher 42 is configured for ejecting an associated surgical fastener 32 towards a corresponding retainer 28 on fastener retaining frame 24. A distal end of a drive shaft is operably connected with annular pusher 40 and a proximal end of the drive shaft is operably connected with trigger 210, whereby actuation of trigger 210 distally advances the drive shaft which advances annular pusher 40 within housing 45 of shell assembly 10 to eject surgical fasteners 32 from fastener guide member 30 in a manner described below. A circular knife 51 with an annular cutting blade is advanced by the pusher 40 to sever tissue in the manner described below.

Figure 3:
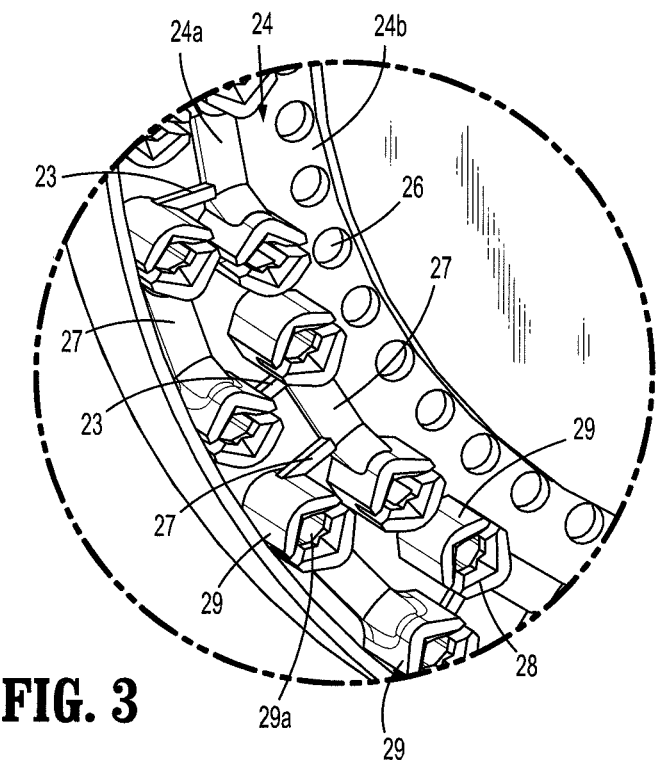
FIG. 3 is an enlarged perspective view of detail area "3" of FIG. 2.
Figure 4:
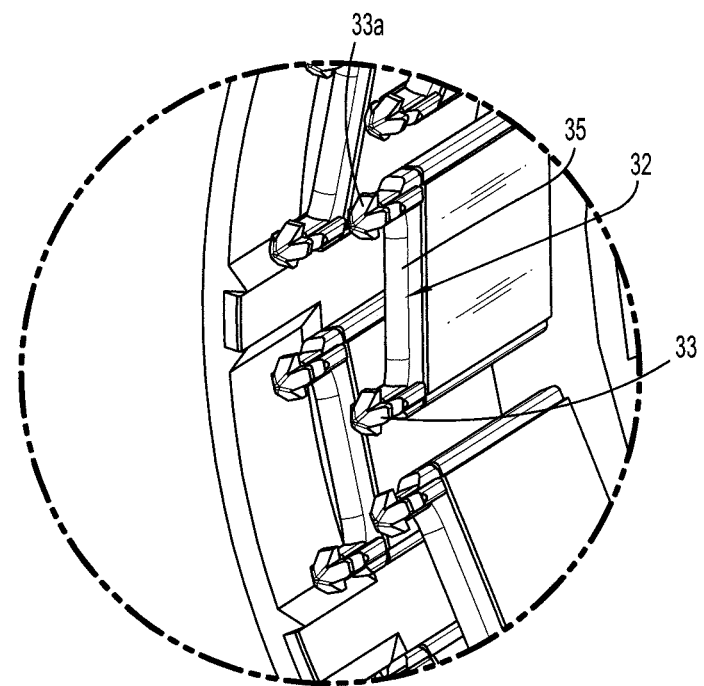
FIG. 4 is an enlarged perspective view of detail area "4" of FIG. 2.
Figure 5:
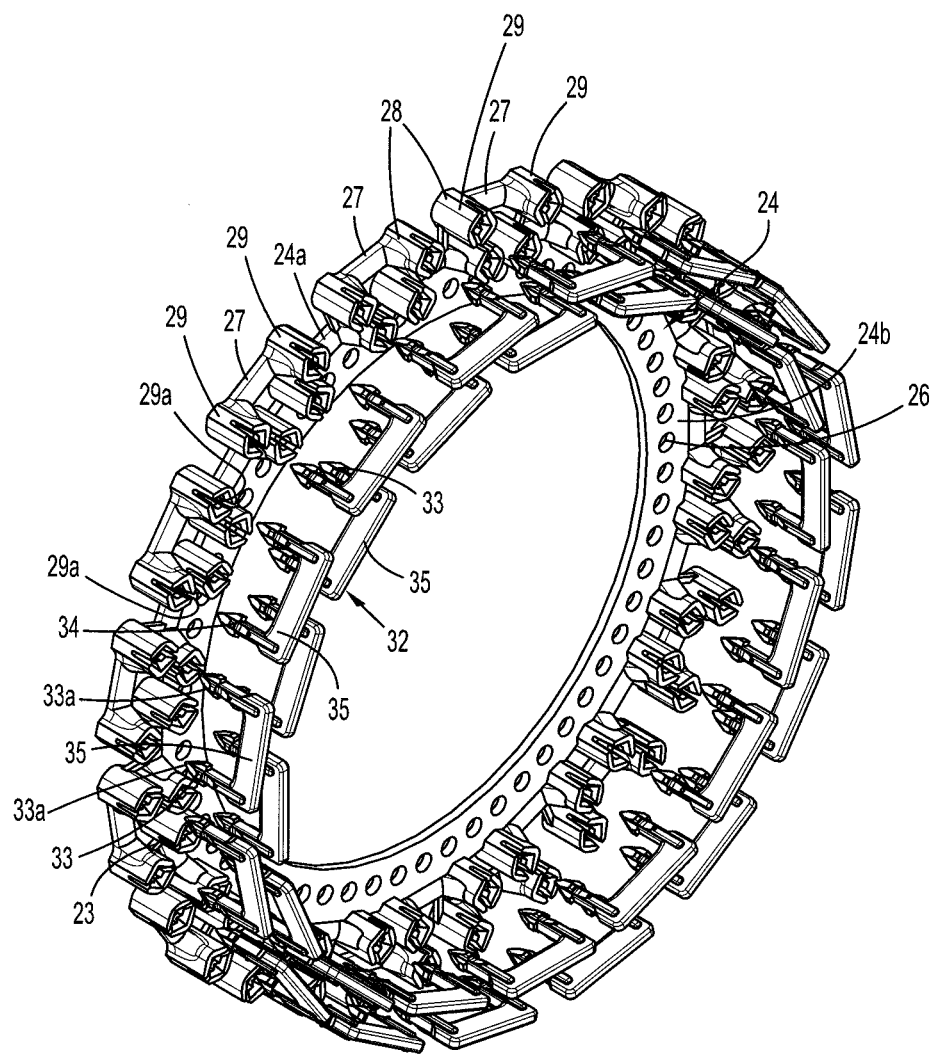
FIG. 5 is a perspective view of the retainer and fastener assembly of FIG. 1.

With particular reference to FIGS. 3 and 5, fastener retaining frame 24 will be described in detail. Fastener retaining frame 24 includes a first annular portion 24a having a plurality of retainers 28 circumferentially disposed thereon and a second annular portion 24b having a plurality of circumferentially arranged perforations 26. The two annular portions 24a and 24b are concentrically arranged, with the second annular portion 24b concentrically arranged within (radially inwardly) of the first annular portion 24a. The plurality of retainers 28 are either monolithically formed or are individually formed and connected by suitable structures, e.g., links 23, thereby forming a single body. Moreover, first annular portion 24a may be monolithically formed with second annular portion 24b. The first annular portion 24a and the second annular portion 24b may be made of different materials, but in some embodiments they are made of biodegradable polymers (e.g. L4). For clarity, only a few of the retainers, perforations, etc. are labeled.

Figure 7:
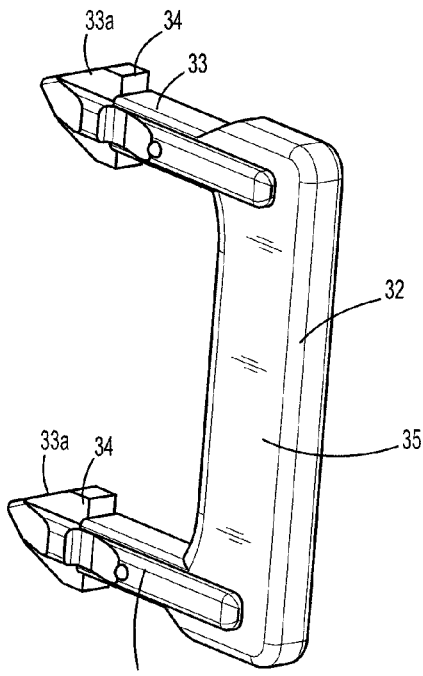
FIG. 7 is a perspective view of a fastener in accordance with one embodiment of the present disclosure.
Figure 9:
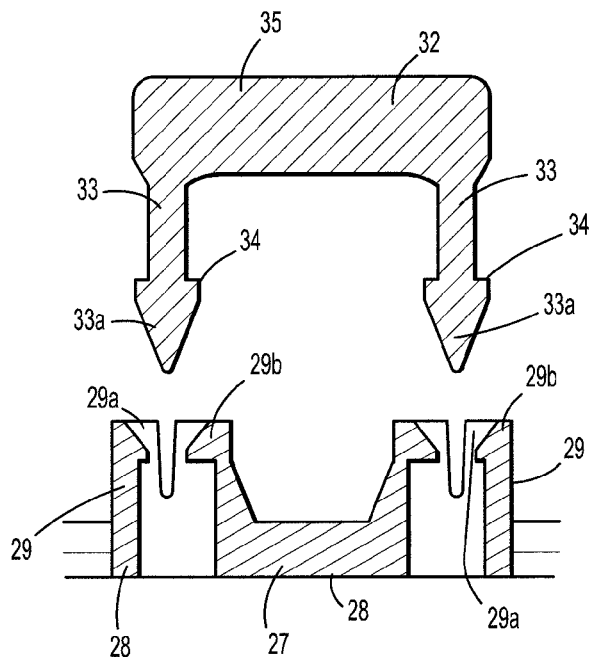
FIGS. 9-11 illustrate the movement of the fastener of FIG. 7 into locking engagement with a retainer of the present disclosure.

With reference still to FIGS. 3 and 5, each retainer 28 includes a bridge or backspan 27 and a pair of posts 29 each forming a cavity or opening 29a therein. Each retainer 28 is mated with an associated surgical fastener 32. Specifically, each prong 33 (FIG. 7) of the associated surgical fastener 32 is inserted into each cavity 29a of associated retainer 28. Surgical fastener 32 and retainer 28 may be configured to engage in a snap-fit manner. This is described in detail below with reference to FIGS. 9-11. Furthermore, a tip 33a of each prong 33 may include a barb 34 to enhance secure mating with retainer 28. Bridge or backspan 35 extends between prongs 33. The plurality of retainers 28 circumferentially disposed on first annular portion 24a of fastener retaining frame 24 are arranged to define a ring of retainers 28. The first annular portion 24a includes two rings of retainers 28 wherein each ring has 16 retainers, although a different number of retainers and/or a different number of rings are contemplated. When more than one ring of retainers 29 is present in first annular portion 24a, retainers 28 forming one ring may be radially aligned with those forming another ring. Alternatively, retainers 28 forming one ring may have a partial overlap or be radially offset with those forming another ring. Retainers 28 may be substantially uniformly spaced apart; however, the spacing between retainers 28 may be tailored to meet the specific needs of the surgical operation being performed. The fasteners 32 and retainers 28 are preferably made of a resorbable material.

Figure 8:
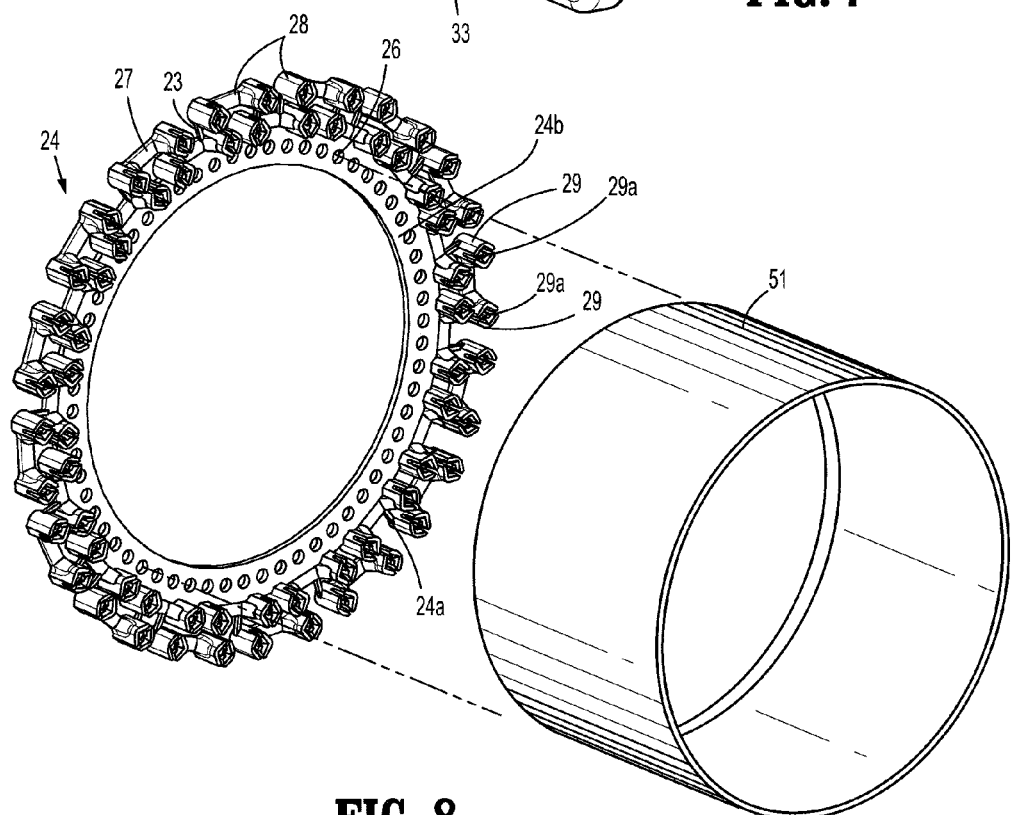
FIG. 8 is a perspective view of the retainer assembly and knife of the apparatus of FIG. 1.

With reference still to FIGS. 3, 5 and 8, fastener retaining frame 24 includes a plurality of perforations 26 in second annular portion 24b thereof. The plurality of perforations 26 may be substantially uniformly formed (substantially uniformly spaced apart) in second annular portion 24b. As an alternative to equidistant or substantially equidistant spacing, other spacing for the perforations 26 is also contemplated including perforations 26 arbitrarily defined or otherwise spaced. In one embodiment, the plurality of perforations 26 may define more than one ring of perforations. The diameter of each of the plurality of perforations 26 may be selected such that the thickness of the annular blade is less than the diameter of each of perforations 26. Such configuration may facilitate severing or breaking off of the plurality of perforations 26. In addition, each perforation 26 may include a radially notched portion configured to facilitate severing or breaking off of perforations 26 upon actuation of annular pusher 40. Alternatively, each perforation 26 may include a pair of opposing slits also serving to facilitate breaking off of perforations 26 upon actuation of annular pusher 40. When employing perforations 26 containing for example the pair of slits, the width of the slits may be chosen to correspond with the thickness of the annular blade to allow the annular blade to be engaged within the opposing slits of the associated perforation. In some embodiments, the thickness of second annular portion 24b defining the plurality of perforations 26 may be varied. For example, an inner part of the second annular portion 24b, i.e., a part that is inside of the plurality of perforations 26, can have a thickness less than that of an outer part of second annular portion 24b, i.e., a part that is in contact with first annular portion 24a, whereby the relatively thinner part or more brittle part can serve to facilitate breaking off of perforations 26 resulting in a detachment of fastener retaining frame 24 from flange member 16 as will be discussed below. In the alternative, the thickness of only a part defining the plurality of perforations 26 may be less than that of the rest of second annular portion 24b whereby such configuration also facilitates breaking off of the plurality of perforations 26 resulting in a detachment of fastener retaining frame 24 from flange member 16.

Figure 12:
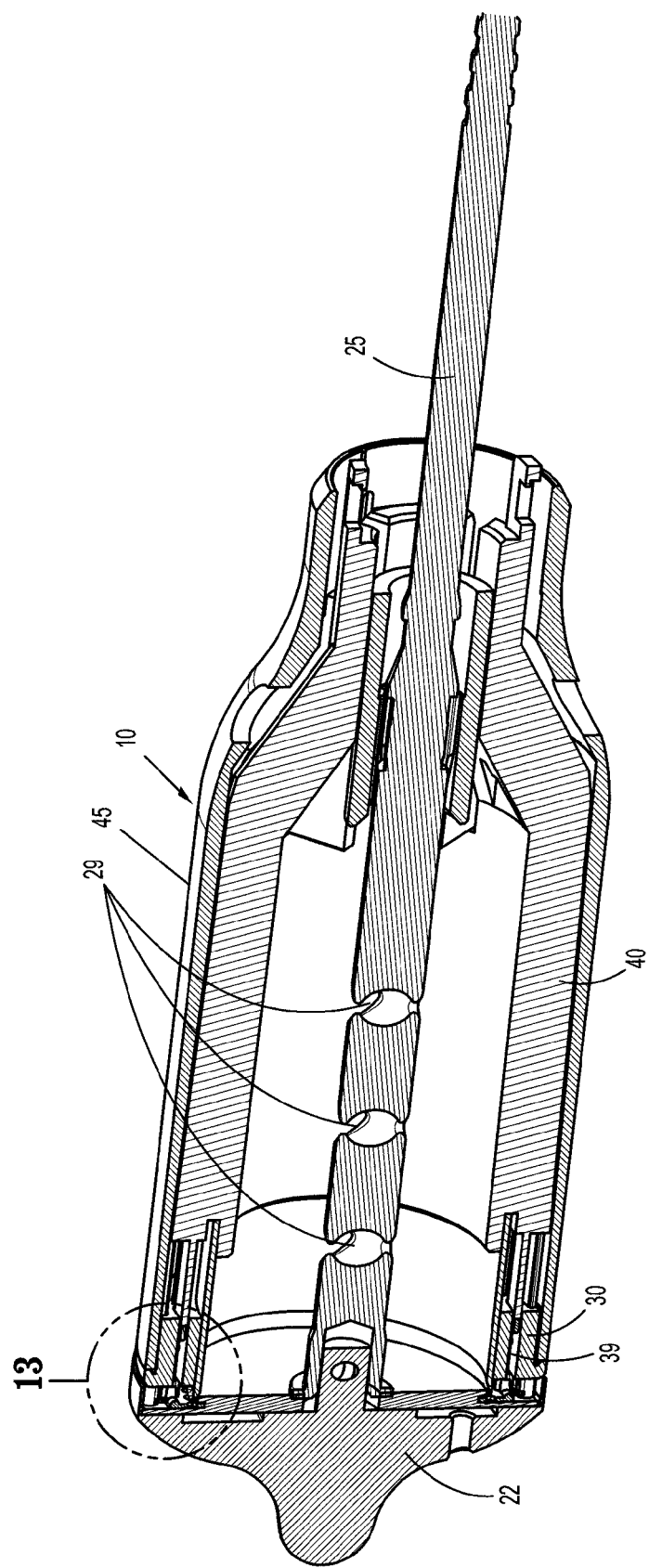
FIG. 12 is a longitudinal cross-sectional view of the end effector of FIG. 1.
Figure 13:
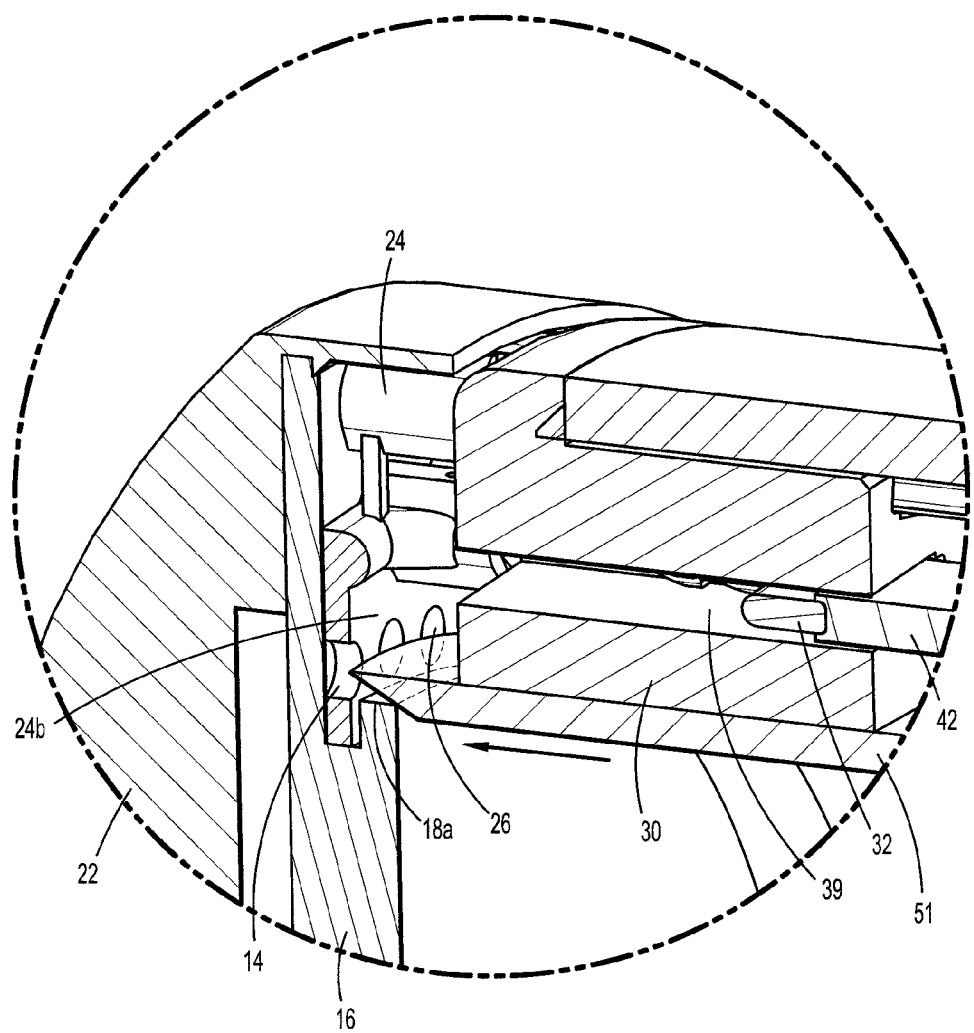
FIG. 13 is an enlarged view of detail area "13" of FIG. 12.

Turning to FIGS. 12 and 13, anvil assembly 20 in a closed position prior to the firing of surgical fasteners 32 by the actuation of trigger 210 is illustrated. Flange member 16 has an annular recess 18 and includes a ledge 18a to form a supporting and/or retaining structure to fastener retaining frame 24. Fastener retaining frame 24 is disposed in annular recess 18 and is secured therein by ledge 18a. FIG. 13 illustrates ledge 18a securing fastener retaining frame 24 at second annular portion 24b. Accordingly, the thickness of the inner part of second annular portion 24b and/or the rigidity of second annular portion 24b may be chosen, e.g., by choosing the material having the requisite rigidity, to prevent bending of the mated fastener retaining frame 24 at perforations 26 and/or at a location in contact with ledge 18a prior to severing the plurality of perforations 26. In one embodiment, a distal side of fastener retaining frame 24 is axially tapered with respect to the thickness thereof to enhance secure attachment thereof to annular recess 18 of flange member 16 also axially tapered with respect to the thickness thereof. Flange member 16 having fastener retaining frame 24 detachably secured thereto is fixedly attached to anvil 22 so that fastener retaining frame 24 and anvil 22 move as a single unit in an longitudinal translation thereof through a manual operation of the rotational knob 220 by the operator.

Still referring to FIGS. 12 and 13, shell assembly 10 accommodates fastener guide member 30 which contains a plurality of circumferentially arranged and axially extending fastener slots 39 for receiving therein a plurality of axially extending surgical fasteners 32 having tissue piercing prongs 33 for mating with plurality of retainers 28 on fastener retaining frame 24 to fasten body tissue therebetween. FIGS. 12 and 13 illustrate a surgical fastener 32 loaded in fastener slot 34 and having a proximal side thereof engaged with an associated pusher 42 prior to being fired.

In use, anvil assembly 20 is spaced from shell assembly 10 as shown in FIG. 1 such that the end effector is an open or unapproximated position. Once the body tissues to be fastened are placed in the open space between anvil assembly 20 and shell assembly 10, anvil assembly 20 is translated proximally to an approximated position to clamp the body tissues therebetween such that the end effector is in a closed or approximated position. This is achieved by rotating the rotatable knob 220 of the handle assembly 200.

Figure 10:
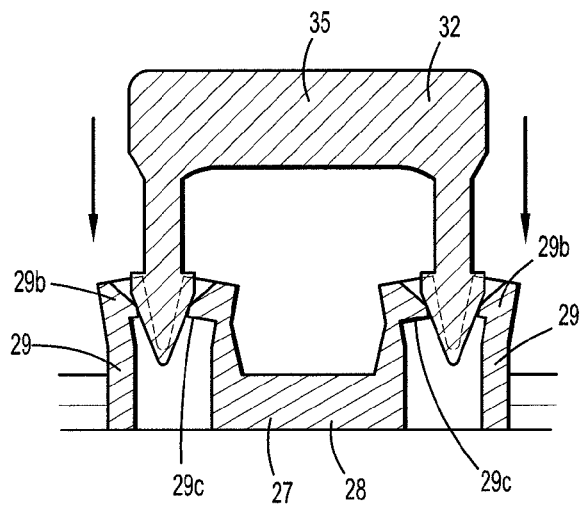
Figure 11:
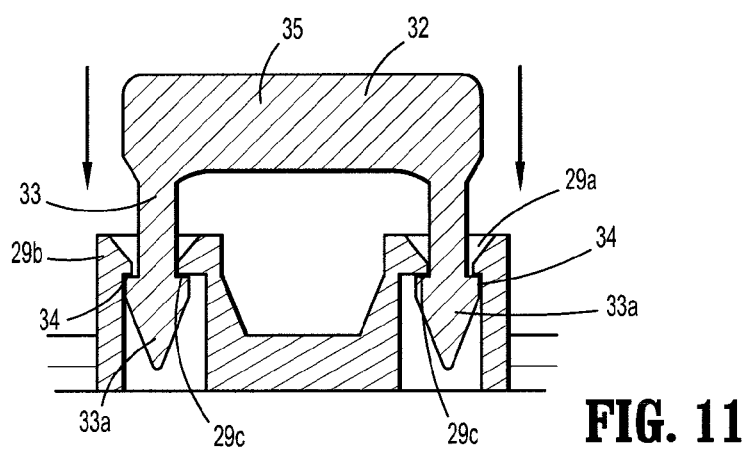

The attachment of fastener retaining frame 24 to flange member 16, which is fixedly attached to anvil 22, reduces slippage of fastener retaining frame 24 against anvil 22 and retains its position with respect to anvil 22 during axial translations thereof. Once the clamping of the body tissues has taken place, the operator actuates trigger 210 which in turn distally drives the drive shaft connected to annular pusher 40. The plurality of pushers 42 on the distally translated annular pusher 40 ejects the corresponding set of surgical fasteners 32 from fastener slots 34 of fastener guide member 30. Each of the ejected set of surgical fasteners 32 pierce through the body tissue and are received into a corresponding retainer 28. Specifically, a portion of each of the prongs of fasteners 32 is received into a respective cavity 29a formed in posts 29 in retainer 28. This is shown in the fastener advancement steps of FIGS. 9-11 wherein the tip 33 and barbs 34 of fastener prong 33 deform receiving walls 29b of posts 29 as the fastener prong 33 is forced through cavity 29a as shown in FIG. 10. After passage beyond receiving walls 29b, the barbs 34 of fastener 32 engage ledge 29c of wall 29b to prevent retraction (proximal movement) of the fastener 32, thereby locking the fastener 32 with the respective retainer 28.

Note that since fastener retaining frame 24 is securely attached to flange member 16 which is fixedly attached to anvil 22, slippage of fastener retaining frame 24 against anvil 22 due to the firing force produced by the actuation of trigger 210 which ejects the plurality of fasteners 32 from fastener slots 34 into the body tissues is reduced. Thus, the position of fastener retaining frame 24 is maintained with respect to anvil 22 during the firing of surgical fasteners 32. Moreover, the plurality of retainers 28 are either monolithically formed or individually formed and connected by suitable structures, e.g., links, thereby forming a single body. In either instance, the configuration of the plurality of retainers 28 as a single body, in conjunction with fastener retaining frame 24 being secured to flange member 16 which is fixedly attached to anvil 22, reduces the radial misalignment of surgical fasteners 32 with fastener retaining frame 24.

Figure 14:
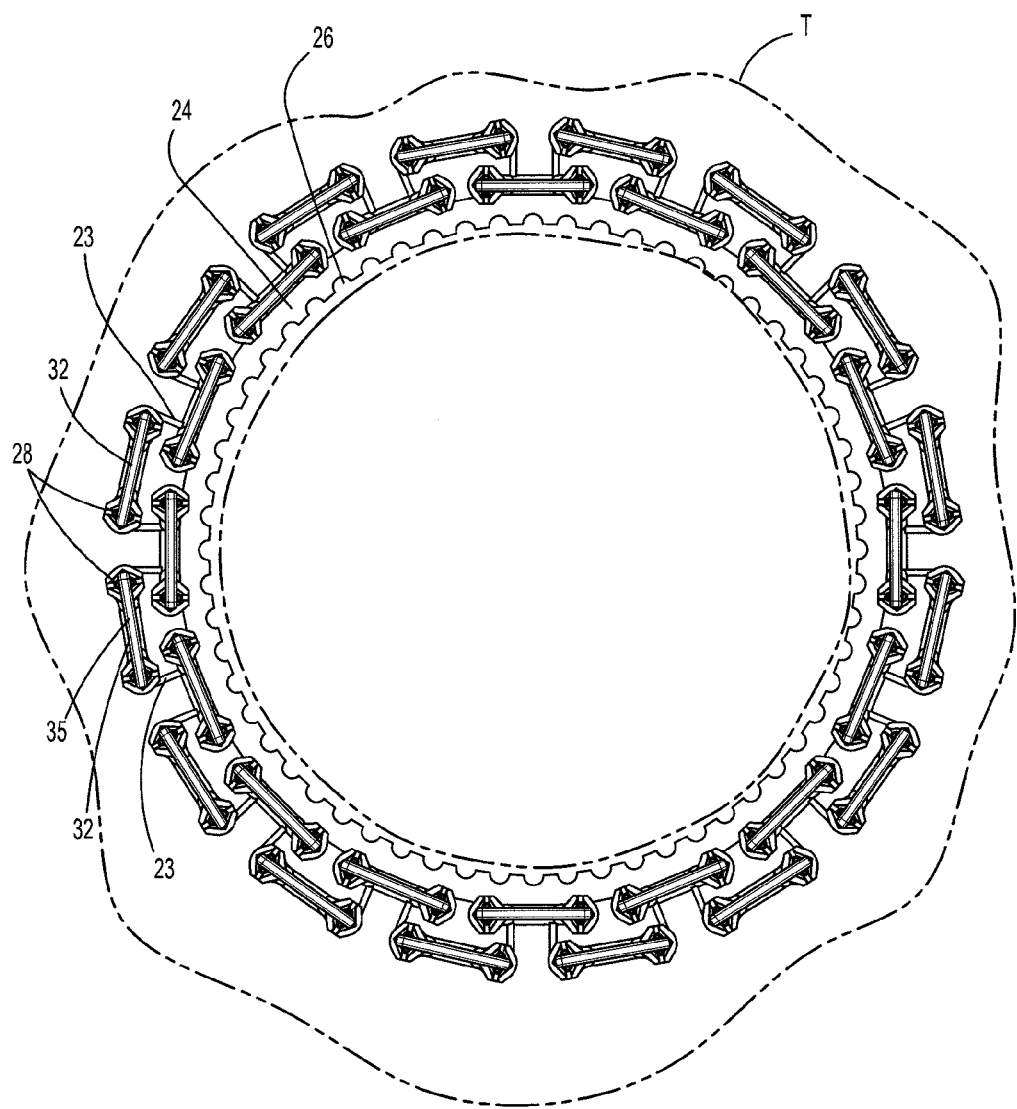
FIG. 14 is a front view illustrating the severing of the fastener retaining frame.

As noted above, fastener retaining frame 24 and fastener guide member 30 may be configured to provide a plurality of rings of surgical fasteners 32 on tissue, e.g., two rings of surgical fasteners wherein each ring is defined by sixteen fasteners, to meet the needs of the specific procedure being performed. Upon mating of the plurality of surgical fasteners 32 with fastener retaining frame 24, an annular blade 51 is actuated to distally translate through shell assembly 10. Note the annular blade can be translatable by actuation of the trigger 210 which advances the fasteners, or alternatively by a separate actuator actuated in a separate step. The annular blade 51 comes into contact with fastener retaining frame 24 and is pressed against the plurality of perforations 26 defined in the fastener retaining frame 24 severing or breaking perforations 26. This is illustrated in FIG. 14 showing the broken fastener retaining frame 24 after the fasteners are applied through tissue T. The broken or severed perforations 26 enable the mated surgical fastener 32 and fastener retaining frame 24 to be detached from anvil 22. The severing or breaking off of perforations 26 leaves a residuary ring, i.e., the inner part of second annular portion 24b of fastener retaining frame 24 (see FIG. 14), within ledge 18a of annular recess 18 of flange member 16. In some embodiments, in order to prevent perforation chips that may be produced during the severing or breaking off of perforations 26, each of the plurality of perforations 26 may be provided with, for example, a pair of opposing slits or a notched portion, as mentioned above, wherein the thickness of the annular blade is chosen to be smaller than, e.g., the width of the pair of opposing slits. The mated surgical fastener 32 and fastener retaining frame 24 fastening body tissue therebetween would then be free to displace without being restricted or attached to anvil 22. Actuation of the knife severs the tissue. The operator then moves anvil 22 to the open position by rotating the rotatable knob 220 of the handle assembly thereby distally translating anvil assembly 20. After the removal of the severed tissue, e.g. hemorrhoidal tissue, surgical fastening device is extracted from the body.

FIGS. 15 and 16 illustrate an alternate embodiment of the present disclosure. An apparatus such as that of FIG. 1 or in the patents/application referred to above and incorporated herein by reference can be utilized for approximation and fastener firing. A fastener receiving frame or plate 80 has a plurality of spaced apart openings 82 formed therein. The frame 80 is preferably substantially annular in configuration and the openings 82 are preferably substantially equidistantly spaced, although other frame shapes and different spacings of the openings are also contemplated. The frame 80 can be formed of an elastic material to provide some bending/flexibility of the frame 80. The fastener receiving frame 80 is preferably composed of a bioabsorbable material. The fastener receiving frame 80 is preferably detachably secured to an anvil similar to anvil 22 of FIG. 1 via engagement with a flange member similar to flange member 16 of FIG. 6.

A fastener supporting member or plate 90, preferably substantially annular in configuration, contains a plurality of spaced apart fasteners 92 extending therefrom. The fasteners 92 are illustratively substantially equidistantly spaced along the frame 90 to correspond to the spacing of the openings 82 in frame 80. It is contemplated that other spacings of the fasteners 92 and openings 82, including non-uniform spacings, are also contemplated.

The fastener assembly of FIGS. 15 and 16 is designed to enable engagement of the fasteners and frame 80 at various depths to accommodate different tissue thickness. One way this is achieved is by the series of axially spaced locking tabs 94 along the length of the fastener 92. In the illustrated embodiment, four locking tabs 94 are shown spaced along the longitudinal axis of the fastener 92, it being understood however, that a different number of locking tabs can be provided as well as different spacings, e.g. non-uniform spacings. As shown in FIG. 16, the locking tabs 94 extend radially from the fastener support member 90 and engage an internal wall 84 within opening 82. In this manner, the fastener can mate with the frame 80 at various depths, depending on which tab 94 engages the ledge 84a of internal wall 84. In FIG. 16, the second locking tab 94 (from the tip) is shown engaged. Fasteners 92 can also include a longitudinal slot 95 separating each fastener 92 into two identical half portions. In such structure, the locking tabs 94 are hemispherical shaped, with four on each fastener half. This provides for increased flexibility of the fastener 92 as it is inserted through opening 80 and past the internal wall 84 of the opening 82.

The projecting surfaces, e.g. tabs 94, can also have an angled surface 96 to enable movement of the fastener in a direction toward the frame 80 while the straight surface 97 prevents movement in a reverse direction (away from the fastener receiving frame 80).

In use, after the fastener receiving frame 80 and fastener supporting member 90 are approximated to clamp tissue therebetween by a knob such as rotatable knob 220 of FIG. 1, a pusher is actuated by a trigger such as trigger 210 of FIG. 1, to advance the fastener supporting member 90 distally as a unit to advance the fasteners 92 as a unit.

If thicker tissue is encountered, then the extent of penetration of the fasteners 92 into openings 82 will be less than if thicker tissue is encountered. This will enable fastening the two members 80, 90 without overcompressing tissue which can cause tissue trauma and other adverse effects. If thinner tissue is encountered, then the fasteners 92 can penetrate to a greater depth (level) within the respective opening 80, thus providing secure engagement.

The fastener support frame 90 can be composed of an elastic material so that it can flex during application to tissue. In this manner, accommodation can be made for varying tissue thicknesses of the tissue clamped between frames 80 and 90. For example, if a first region of the clamped tissue is thicker than a second region, the frame 90 can flex so that fasteners 92 adjacent the second region can penetrate a greater depth than fasteners 92 adjacent the first region and a different locking tab 94 can locking engage the wall 84. Fastener receiving frame 80 can also be composed of an elastic material to provide bending/flexibility.

Although locking tabs are shown on the fasteners 92, it is also contemplated that the openings 82 can be configured with tabs, walls or other structure at various "levels" to provide the locking structure.

An annular cutting blade, similar to blade 51 of FIG. 6, can be provided to sever tissue.

Figure 17:
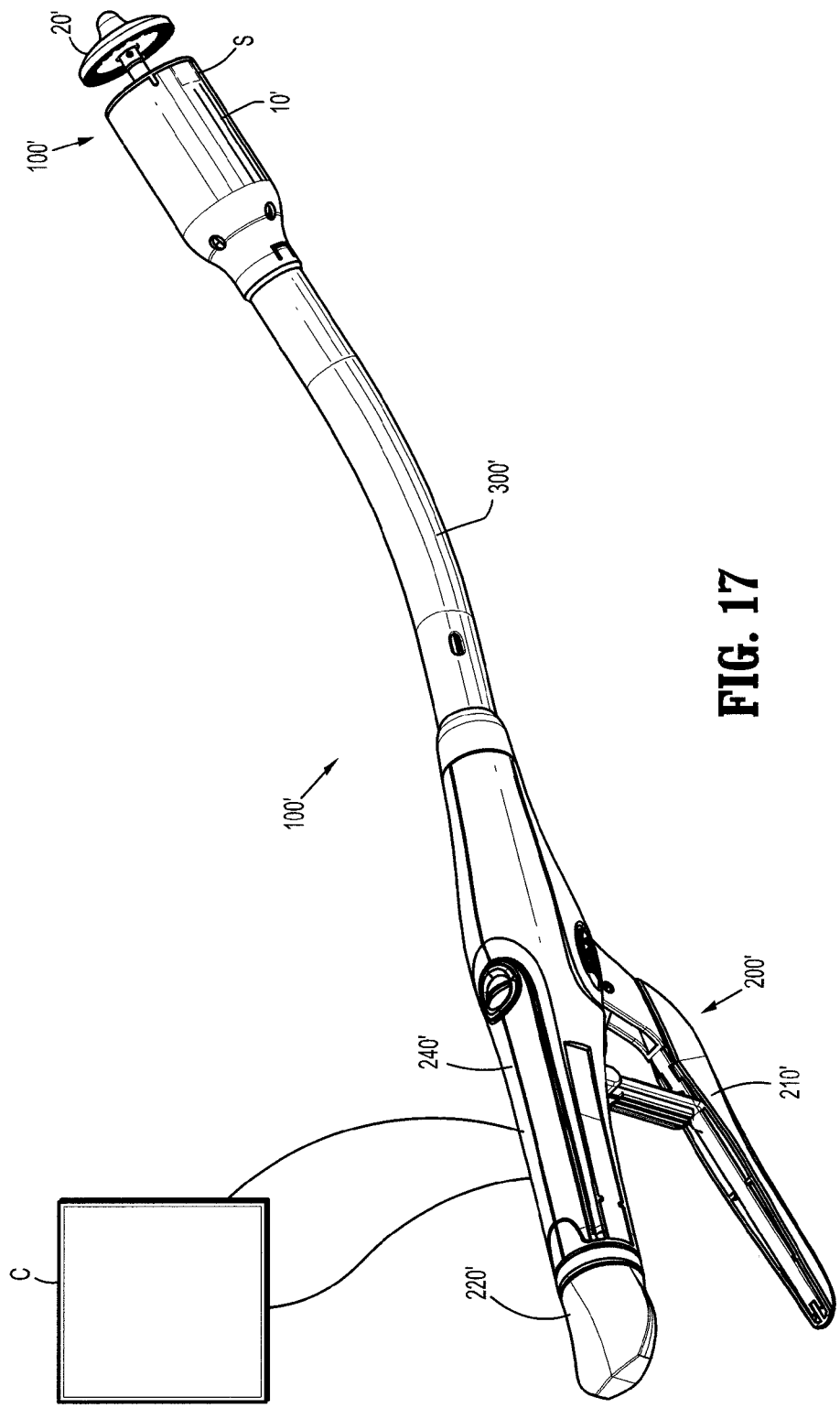
FIG. 17 is a perspective view of an alternate embodiment of the surgical fastening apparatus.

In alternative embodiments, the depth of the fasteners can be preset prior to firing the fasteners. That is, the fastener pusher would be preset to the distance of travel to accommodate the desired degree of advancement of the fastener supporting member and fasteners into the openings 82 of the fastener receiving frame 80. Additionally, several pushers could be provided, e.g. arranged in quadrants or other regional separations, so that each of the pushers could be preset so that various pushers can be advanced to various depths. This can be achieved by placement of a sensor adjacent the end effector at the distal portion of the apparatus which can measure a tissue parameter, e.g. tissue thickness, and/or measure an end effector parameter at the distal portion of the apparatus, e.g. the gap between the fastener receiving frame 80 and fastener supporting frame 90 once approximated to clamp tissue therebetween. The sensor sends a signal to a controller which sends a signal to the pusher to control the extent of advancement of the pushers and thus the extent of advancement of fasteners 92 in response to the parameter determined by the sensor. For example, as shown in FIG. 17, apparatus 100' is identical to apparatus 100 of FIG. 1, and corresponding parts are labeled with "prime" designations. Sensor S in this embodiment measures the gap between shell assembly 10' and anvil assembly 20' of end effector 100', sending a signal (via wires internal of the shaft 300') to controller C. Controller C sends a signal via the wire to the actuator within the handle assembly 200' which sets the distal movement of the actuator in response to the measured parameter. Note that wireless transmissions are also contemplated.

The foregoing embodiments for the fastening receiving frame and fastening supporting frame can be used with the instrument of FIG. 1 described above and in the instruments of U.S. Pat. Nos. 7,168,604, 7,303,106 and application Ser. No. 12/550,443, incorporated by reference hereinabove in their entirety.

The apparatus described herein can be used in various surgical procedures, including for example, hemorrhoid surgery.

From the foregoing and with reference to the various figure drawings, those skilled in the art will appreciate that certain modifications can also be made to the present disclosure without departing from the scope of the same. For example, the annular blade may be fixedly secured to the anvil and configured to break the plurality of perforations on the fastener retaining frame upon firing of the plurality of fasteners. Such design eliminates the need for a longitudinal translation of the annular blade. Although the illustrative embodiments of the present disclosure have been described herein with reference to the accompanying drawings, the above description, disclosure, and figures should not be construed as limiting, but merely as exemplary of various embodiments.

What is claimed is:

1. A surgical fastening assembly comprising:
    a fastener receiving frame having a first annular portion and a second annular portion, the first annular portion defining a plurality of openings and the second annular portion defining a plurality of perforations, and a locking structure supported within each of the plurality of openings;
    a fastener supporting member including a plurality of surgical fasteners, each of the surgical fasteners including at least one projecting surface which is independently engageable with the locking structure supported within a respective one of the plurality of openings to fasten the fastener receiving frame in relation to the fastener supporting member;
    a pusher for advancing the fastener supporting member into engagement with the fastener receiving frame; and
    an annular blade advanceable by the pusher to sever tissue, the annular blade defining a thickness, the plurality of perforations each defining a diameter, wherein the thickness of the annular blade is less than the diameter of each of the plurality of perforations,
    wherein the first and second annular portions are concentric and the plurality of perforations facilitate separation of the first annular portion from the second annular portion.

2. The surgical fastening assembly of claim 1, wherein the second annular portion is positioned radially inwardly of the first annular portion.

3. The surgical fastening assembly of claim 1, wherein the first annular portion and the second annular portion include different materials.

4. The surgical fastening assembly of claim 1, wherein the first annular portion and the second annular portion are made of biodegradable polymers.

5. The surgical fastening assembly of claim 1, wherein the at least one projecting surface includes a plurality of projecting surfaces, each of the projecting surfaces being independently engageable with the locking structure supported within a respective one of the plurality of openings to fasten the fastener receiving frame in relation to the fastener supporting member in a plurality of positions dependent on a thickness of tissue to be fastened.

6. The surgical fastening assembly of claim 5, wherein the plurality of projecting surfaces includes a series of locking tabs spaced along the fastener to mate with the locking structure of the fastener receiving frame within the respective opening at various positions to provide a variable depth of engagement.

7. The surgical fastening assembly of claim 5, wherein the locking structure includes a series of locking surfaces to engage the plurality of projecting surfaces of the respective fastener at various positions to provide a variable depth of engagement.

8. The surgical fastening assembly of claim 6, wherein the locking tabs include a plurality of semi-circular ribs.

9. The surgical fastening assembly of claim 8, wherein each of the fasteners includes a longitudinally extending slot formed therein.

10. The surgical fastening assembly of claim 6, wherein the locking tabs include a plurality of projections angled to enable movement of the fastener in a first direction into the opening in the fastener receiving frame and prevent movement of the fastener in a second direction away from the opening.

11. The surgical fastening assembly of claim 5, wherein the fasteners include a reservoir to receive a drug.

12. The surgical fastening assembly of claim 5, wherein the fastener receiving frame has a planar outer surface.

13. The surgical fastening assembly of claim 5, wherein each of the openings has a first depth and the respective fastener has a first length, the first length being less than the first depth.

14. The surgical fastening assembly of claim 1, wherein the plurality of perforations are uniformly defined in the second annular portion.

15. The surgical fastening assembly of claim 1, wherein the plurality of perforations are nonuniformly defined in the second annular portion.

16. The surgical fastening assembly of claim 1, wherein the plurality of perforations define a ring of perforations.

17. The surgical fastening assembly of claim 1, wherein the plurality of perforations define a plurality of rings of perforations.

18. The surgical fastening assembly of claim 1, wherein each of the plurality of perforations includes a notch that extends along a direction parallel to the outer periphery of the second annular portion.

19. The surgical fastening assembly of claim 1, wherein each of the plurality of perforations includes a slit having a pair of opposite ends.

20. The surgical fastening assembly of claim 19, wherein each slit has a width which corresponds to the thickness of the annular blade.

\* \* \* \* \*